(12) United States Patent
McKinley et al.

(10) Patent No.: US 11,211,166 B2
(45) Date of Patent: Dec. 28, 2021

(54) METHODS AND SYSTEMS FOR TISSUE DAMAGE IDENTIFICATION AND QUANTIFICATION

(71) Applicant: Indiana University Research and Technology Corporation, Indianapolis, IN (US)

(72) Inventors: Todd O. McKinley, Indianapolis, IN (US); Scott D. Steenburg, Zionsville, IN (US)

(73) Assignee: Indiana University Research & Technology Corp, Indianapolis, IN (US)

( * ) Notice: Subject to any disclaimer, the term of this patent is extended or adjusted under 35 U.S.C. 154(b) by 1365 days.

(21) Appl. No.: 14/851,799

(22) Filed: Sep. 11, 2015

(65) Prior Publication Data

US 2016/0078187 A1  Mar. 17, 2016

Related U.S. Application Data

(60) Provisional application No. 62/049,699, filed on Sep. 12, 2014.

(51) Int. Cl.
*G16H 50/20* (2018.01)
*G16H 50/30* (2018.01)
*G16H 30/40* (2018.01)

(52) U.S. Cl.
CPC ............. *G16H 50/20* (2018.01); *G16H 30/40* (2018.01); *G16H 50/30* (2018.01)

(58) Field of Classification Search
CPC ........ G16H 50/20; G16H 50/30; G06F 19/00; G06F 19/321

USPC .......................................................... 705/2, 3
See application file for complete search history.

(56) References Cited

U.S. PATENT DOCUMENTS

2008/0108894 A1* 5/2008 Elgavish .............. G06T 19/00
                                              600/420

OTHER PUBLICATIONS

Alam, Mohammad Shaha, Multiple Organ Dysfunction Syndrome In Major Burns Patients, 2010, Bangladesh Journals Online, vol. 22 No 2 https://www.banglajol.info/index.php/MEDTODAY/article/view/12438 (Year: 2010).*
Pittet, D., Rangel-Frausto, S., Li, N. et al. Intensive Care Med (1995) 21: 302. https://doi.org/10.1007/BF01705408; "The Severity of Injury and the Extent of Hemorrhagic Shock Predict the Incidence of Infectious Complications in Trauma Patients," (Year: 1995).*
Frantz et al., "Tissue damage volume predicts organ dysfunction and inflammation after injury", Journal of Surgical Research. (Year: 2015).*

(Continued)

*Primary Examiner* — Joshua B Blanchette
(74) *Attorney, Agent, or Firm* — Barnes & Thornburg LLP

(57) ABSTRACT

Example embodiments are described that relate to the analysis of tissue damage in an injured patient. Example embodiments are methods and systems for collecting medical imaging data, identifying tissue damage in the medical imaging data, analyzing the tissue damage shown in the medical imaging data, and/or quantifying the tissue damage shown in the medical imaging data. The disclosed methods allow for determining a risk for multiple organ failure and systemic inflammation in a multiply injured patient.

7 Claims, 6 Drawing Sheets

(56) References Cited

OTHER PUBLICATIONS

Jacobs et al., "Computed Tomography and Outcome in Moderate and Severe Traumatic Brain Injury: Hematoma Volume and Midline Shift Revisited", Journal of Neurotrauma 28:203-215 (Feb. 2011) (Year: 2011).*

Pittet, D., Rangel-Frausto, S., Li, N. et al. Intensive Care Med (1995) 21: 302. https://doi.org/10.1007/BF01705408; "The Severity of Injury and the Extent of Hemorrhagic Shock Predict the Incidence of Infectious Complications in Trauma Patients," (Year: 1995).*

Gardner et al., "Volume Measures Using a Digital Image Analysis System are Reliable in Diabetic Foot Ulcers", Wounds. 2012;24(6): 146-151. (Year: 2012).*

Albouy B. et al., "Volume Estimation from Uncalibrated Views Applied to Wound Measurement," ICIAP 2005, LNCS 3617, pp. 945-952, 2005. (Year: 2005).*

Chawda et al., "Predicting outcome after multiple trauma:which scoring system?", Injury, Int. J. Care Injured (2004)35, 347-358 (Year: 2004).*

* cited by examiner

METHODS AND SYSTEMS FOR TISSUE DAMAGE IDENTIFICATION AND QUANTIFICATION

CROSS-REFERENCE TO RELATED APPLICATIONS

This application claims the benefit under 35 U.S.C. § 119(e) of U.S. Provisional Application Ser. No. 62/049,699, filed Sep. 12, 2014, the disclosure of which is incorporated herein by reference in its entirety.

BACKGROUND

The field of the disclosure relates to methods and systems for identifying, analyzing, and/or quantifying tissue damage based on medical imaging data.

Multiply injured patients are at risk to develop severe systemic inflammation which can lead to organ failure, chronic illness, and death. It is difficult to predict which patients will have post-injury complications and are at the greatest risk of systemic inflammation and organ failure. Current evidence supports the belief that molecules released from damaged tissue incite and propagate internal mechanisms that cause systemic inflammation.

BRIEF DESCRIPTION

One aspect of the present disclosure is an analytical system for use in analyzing tissue injuries shown in medical image data. The system includes a memory device and a processor communicatively coupled to the memory device. The system is programmed to determine, from medical image data of a patient, a tissue injury index based at least in part on a total volume of tissue injury for the patient.

Another aspect of this disclosure is directed to a method for determining a risk for multiple organ failure in an injured patient. The method includes: obtaining a medical image of a plurality of tissue injuries; calculating a volume measurement for each of the plurality of tissue injuries; summing the volume measurement for each of the plurality of tissue injuries to determine a total volume of tissue injury; and determining a risk for multiple organ failure of the injured patient based on the summed volume measurement.

Another aspect of this disclosure is directed to a method for determining a risk for systemic inflation in an injured patient. The method includes: obtaining a medical image of a plurality of tissue injuries; calculating a volume measurement for each of the plurality of tissue injuries; summing the volume measurement for each of the plurality of tissue injuries to determine a total volume of tissue injury; and determining a risk for systemic inflation of the injured patient based on the summed volume measurement.

The features, functions, and advantages that have been discussed can be achieved independently in various embodiments or may be combined in yet other embodiments further details of which can be seen with reference to the following description and drawings.

DETAILED DESCRIPTION

Figure 1:
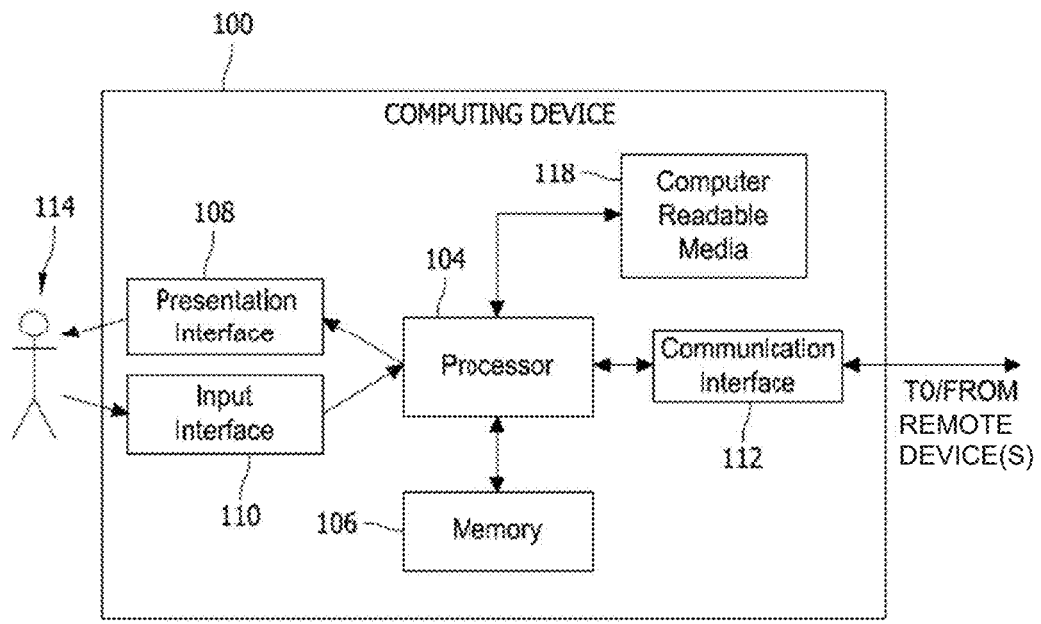
FIG. 1 is a block diagram of a computing device.

The subject matter described herein relates to the analysis of tissue damage in a patient. More particularly, the subject matter relates to methods and systems for collecting medical imaging data, identifying tissue damage in the medical imaging data, analyzing the tissue damage shown in the medical imaging data, and/or quantifying the tissue damage shown in the medical imaging data. The embodiments described herein include a metric to quantify the magnitude (physical volume) of damaged tissue sustained by an injured patient by measuring the volume and type of injured tissue in trauma patients. This index can be used to determine subsequent systemic inflammation and organ dysfunction that occurs after injury. The index provides an early clinical quantity to affect patient care.

The methods of the present disclosure as described herein are intended in some embodiments to include the use of such methods in "at risk" patients, including patients unaffected by or not otherwise afflicted with organ failure, multiple organ failure, and/or systemic inflammation as described herein, for the purpose of diagnosing, prognosing and identifying individuals such that treatment, treatment planning, and treatment options for organ failure, multiple organ failure, and/or systemic inflammation can be made. As used herein, patient "at risk for" organ failure, multiple organ failure, and/or systemic inflammation refers to patients who may develop organ failure, multiple organ failure, and/or systemic inflammation. As such, in some embodiments, the methods disclosed herein are directed to a subset of the general population such that, in these embodiments, not all of the general population may benefit from the methods. Particularly specific subsets of patients suitable for the methods disclosed herein include multiply injured patients and trauma patients. Based on the foregoing, because some of the method embodiments of the present disclosure are directed to specific subsets or subclasses of identified patients (that is, the subset or subclass of individuals "at risk for" the specific conditions noted herein), not all patients will fall within the subset or subclass of patients as described herein.

As used herein, "a multiply injured patient" refers to a patient who has sustained severe injuries (Abbreviated Injury Score of >3) to at least two body regions including head and neck, thorax, abdomen, pelvis and retroperitoneum, and extremities.

As used herein, "high magnitude systemic inflammatory response syndrome (SIRS)" refers to a patient having a SIRS score of at least 4 for a period of at least two days.

As used herein, "sustained SIRS" refers to a patient having a SIRS score of greater than or equal to 3 for a period of at least 5 days.

As used herein, an element or step recited in the singular and proceeded with the word "a" or "an" should be understood as not excluding plural elements or steps unless such exclusion is explicitly recited. Furthermore, references to "one implementation" of the present disclosure or the "exemplary implementation" are not intended to be interpreted as excluding the existence of additional implementations that also incorporate the recited features.

The example methods and systems described herein may be implemented with and/or may include one or more controllers. The controllers may include any suitable combination of analog and/or digital controllers capable of performing as described herein. In some implementations, the controller includes or is embodied in a computing device. FIG. 1 is a block diagram of an exemplary, real-world, physical computing device 100 that may be used in a medical analysis system as described herein. In the exemplary implementation, computing device 100 includes a memory 106 and a processor 104 that is coupled to memory 106 for executing programmed instructions. Processor 104 may include one or more processing units (e.g., in a multi-core configuration). Computing device 100 is programmable to perform one or more operations described herein by programming memory 106 and/or processor 104. For example, processor 104 may be programmed by encoding an operation as one or more executable instructions and providing the executable instructions in memory device 106.

Processor 104 may include, but is not limited to, a general purpose central processing unit (CPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer-readable medium including, without limitation, a storage device and/or a memory device. Such instructions, when executed by processor 104, cause processor 104 to perform at least a portion of the methods described herein. The above examples are exemplary only, and thus are not intended to limit in any way the definition and/or meaning of the term processor.

Memory device 106, as described herein, is one or more devices that enable information such as executable instructions and/or other data to be stored and retrieved. Memory device 106 may include one or more computer-readable media, such as, without limitation, dynamic random access memory (DRAM), static random access memory (SRAM), a solid state disk, and/or a hard disk. Memory device 106 may be configured to store, without limitation, maintenance event log, diagnostic entries, fault messages, and/or any other type of data suitable for use with the methods and systems described herein.

In the exemplary implementation, computing device 100 includes a presentation interface 108 that is coupled to processor 104. Presentation interface 108 outputs (e.g., display, print, and/or otherwise output) information such as, but not limited to, installation data, configuration data, test data, error messages, and/or any other type of data to a user 114. For example, presentation interface 108 may include a display adapter (not shown in FIG. 1) that is coupled to a display device, such as a cathode ray tube (CRT), a liquid crystal display (LCD), a light-emitting diode (LED) display, an organic LED (OLED) display, and/or an "electronic ink" display. In some implementations, presentation interface 108 includes more than one display device. In addition, or in the alternative, presentation interface 108 may include a printer.

In the exemplary implementation, computing device 100 includes an input interface 110 that receives input from user 114. For example, input interface 110 may be configured to receive selections, requests, credentials, and/or any other type of inputs from user 114 suitable for use with the methods and systems described herein. In the exemplary implementation, input interface 110 is coupled to processor 104 and may include, for example, a keyboard, a card reader (e.g., a smartcard reader), a pointing device, a mouse, a stylus, a touch sensitive panel (e.g., a touch pad or a touch screen), a gyroscope, an accelerometer, a position detector, and/or an audio input interface. A single component, such as a touch screen, may function as both a display device of presentation interface 108 and as input interface 110.

In the exemplary implementation, computing device 100 includes a communication interface 112 coupled to memory 106 and/or processor 104. Communication interface 112 is coupled in communication with a remote device, such as another computing device 100, a medical imaging device, etc. For example, communication interface 112 may include, without limitation, a wired network adapter, a wireless network adapter, an instrument input port, and/or a mobile telecommunications adapter.

Instructions for operating systems and applications are located in a functional form on non-transitory memory 106 for execution by processor 104 to perform one or more of the processes described herein. These instructions in the different implementations may be embodied on different physical or tangible computer-readable media, such as memory 106 or another memory, such as a computer-readable media 118, which may include, without limitation, a flash drive, CD-ROM, thumb drive, floppy disk, etc. Further, instructions are located in a functional form on non-transitory computer-readable media 118, which may include, without limitation, a flash drive, CD-ROM, thumb drive, floppy disk, etc. Computer-readable media 118 is selectively insertable and/or removable from computing device 100 to permit access and/or execution by processor 104. In one example, computer-readable media 118 includes an optical or magnetic disc that is inserted or placed into a CD/DVD drive or other device associated with memory 106 and/or processor 104. In some instances, computer-readable media 118 may not be removable.

Figure 2:
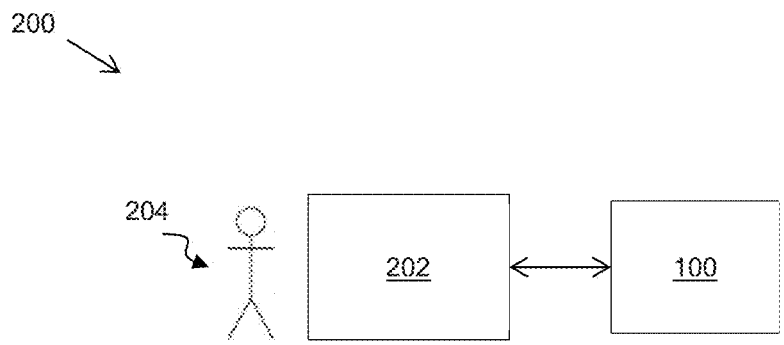
FIG. 2 is an exemplary implementation of a tissue injury analysis system.

FIG. 2 is a simplified diagram of an exemplary implementation of a tissue damage analysis system 200. The system 200 includes a medical imaging system 202 communicatively coupled to computing device 100.

Medical imaging system 202 captures medical image data about a patient 204. Medical imaging system 202 is any suitable system for capturing medically useful images and image data. Medical imaging system 202 may be, for example, a radiography system, a computed tomography (CT) system, a magnetic resonance imaging (MRI) system, an x-ray system, and an ultrasound system. Medical imaging system 202 generates medical image data (e.g., digital medical images) about patient 204 that is provided to computing device 100 for analysis.

The example computing device 100 is remotely located (e.g., in a different room, in a different building, etc.) from medical imaging system 202. Alternatively, computing device 100 may be located near medical imaging system (e.g., in the same room) and/or may be incorporated within medical imaging system 202.

Computing device 100 examines the medical images received from medical imaging system 202 to identify each area of tissue injury shown in the medical images. The area of tissue injury is identified by identifying abnormal gradients on the medical images and, by use of thresholding, circumscribing the injured region identified by the abnormal gradients. Alternatively, the areas of tissue injury may be identified using any suitable image processing technique. Moreover, in some embodiments, user 114 identifies to computing device 100 areas of tissue injury in the medical images in addition to, or in place of, computing device 100 identifying the areas of tissue injury.

Figure 8:
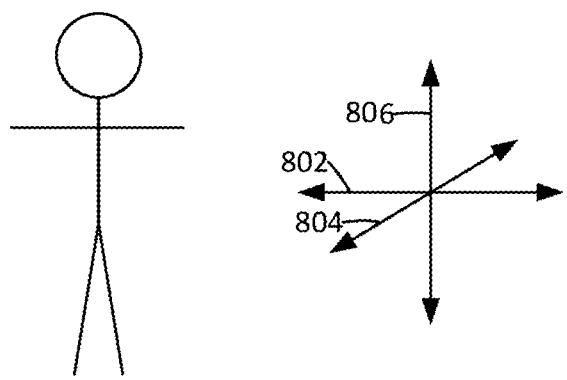
FIG. 8 shows a depiction of measurement axes of a patient and a flow diagram for an exemplary method of taking measurements.
Figure 8:
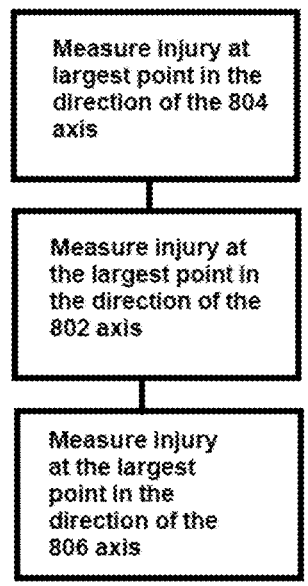

After the areas of tissue injury are identified, computing device 100 determines a volume for each area of injured tissue. Tissue injuries are measured in the maximum axial dimension (i.e., in the direction defined by axis 804 in FIG. 8), followed by a second measurement perpendicular to this axis at the injury's largest point (i.e., in the direction defined by axis 802 in FIG. 8). A third measurement is made in the craniocaudal direction at the injury's largest point (i.e., in the direction defined by the axis 806 in FIG. 8). These three measurements are averaged to calculate a representative diameter of the injury. Each injury is assumed to be spherical and the representative diameter is then used to calculate the total soft tissue injury volume based on the volume formula for a sphere.

Though many injuries conform to a generally spherical shape, not all injuries do so. Some injuries are oval-shaped, some are plate-like, while others are lobular and irregular. Accordingly, in some embodiments, each injury is classified by the shape to which it most conforms. Computing device 100 determines a volume for each tissue injury from its measurements based on its shape classification.

The volume of each injury identified in the medical images is calculated by computing device 100. The volumes of all tissue injuries identified in the medical images are then summed to produce a tissue damage index. The tissue damage index may be referred to as a Total Body Soft Tissue Damage Volume Score or TDVS. Moreover, in some embodiments, the square root of the tissue damage index may be used. The injured tissue measurements may be separated by tissue type and anatomic region in which the injury is located. Different tissue types and or locations may be, additionally or alternatively, summed to produce difference tissue injury indices. In some embodiments, injuries to different types of tissue and/or in different anatomic regions may be given different weights prior to summing the volumes.

Another aspect of this disclosure is directed to a method for determining a risk for systemic inflammation in an injured patient. The method includes: obtaining a medical image of a plurality of tissue injuries; calculating a volume measurement for each of the plurality of tissue injuries; summing the volume measurement for each of the plurality of tissue injuries to determine a total volume of tissue injury; and determining a risk for systemic inflammation of the injured patient based on the summed volume measurement.

The method can further include calculating a diameter measurement of the tissue injury. The diameter can be used to calculate the volume of the tissue injury.

A medical image can be a radiographic image, a computed tomography (CT) scan, a magnetic resonance image (MRI), an x-ray, an ultrasound image, and combinations thereof.

In one embodiment, the injured patient tissue injury can be an axial anatomy tissue injury. A tissue damage volume of an axial anatomy tissue injury from about 1100 ml to about 1750 ml can be used to determine a risk for multiple organ failure in an injured patient.

In another embodiment, the injured patient tissue injury can be a torso tissue injury. A tissue damage volume of a torso tissue injury from about 1000 ml to about 1650 ml can be used to determine a risk for multiple organ failure in an injured patient.

In another embodiment, the injured patient tissue injury can be an abdominopelvis tissue injury. A tissue damage volume of an abdominopelvis tissue injury from about 650 ml to about 1200 ml can be used to determine a risk for multiple organ failure in an injured patient.

In another aspect, the present disclosure is directed to a method for determining a risk for systemic inflammation in an injured patient. The method includes: obtaining a medical image of a plurality of tissue injuries; calculating a volume measurement for each of the plurality of tissue injuries; summing the volume measurement for each of the plurality of tissue injuries to determine a total volume of tissue injury; and determining a risk for systemic inflammation of the injured patient based on the summed volume measurement.

The method can further include calculating a diameter measurement of the tissue injury. The diameter can be used to calculate the volume of the tissue injury.

A medical image can be a radiographic image, a computed tomography (CT) scan, a magnetic resonance image (MRI), an x-ray, an ultrasound image, and combinations thereof.

In one embodiment, the injured patient has high magnitude systemic inflammatory response syndrome.

In one embodiment, the injured patient tissue injury comprises a chest tissue injury. A tissue damage volume of a chest tissue injury from about 425 ml to about 850 ml can be used to determine a risk for multiple organ failure in an injured patient.

In one embodiment, the injured patient has sustained systemic inflammatory response syndrome.

In one embodiment, the injured patient tissue injury comprises a chest tissue injury. A tissue damage volume of a chest tissue injury from about 380 ml to about 750 ml can be used to determine a risk for multiple organ failure in an injured patient.

Any anatomical regions are suitable for analysis according to the methods disclosed herein. Suitable anatomic regions can be categorized into head/neck, chest (thorax), abdomen, pelvis (including retroperitoneum, descending colon, rectum, pelvic bones, bladder, pelvic viscera in women, and genitals) and extremities, for example. Combination regions including, for example, abdominopelvis, torso (chest, abdomen, pelvis) and axial (all anatomic locations: head/neck, chest, abdomen, pelvis) are also suitable.

The tissue damage index is useful to stratify risk in trauma patients and may be used as a clinical diagnostic tool to aid in the care of trauma patients. In some embodiments, computing device 100 determines a risk level for the patient 204 based on the calculated index. The computing device may determine the risk level by comparing the index to a series of predetermined thresholds that correlate to different degrees of risk. In particular, the thresholds may correlate with degrees of risk of systemic inflammation and/or organ failure. The predetermined thresholds are typically derived from statistical analysis of surgical data, autopsy findings, and/or animal models. In other embodiments, computing device 100 presents the tissue damage index to user 114 without comparing the index to thresholds.

In an exemplary embodiment, tissue damage volume can be measured by inspecting orthogonal CT scan sections to determine a characteristic radius of each injury and calculating an injury volume assuming each injury is spherical using the sphere volume equation (I):

$$V = 4/3 r^3 \pi \qquad \text{(I)}.$$

In another exemplary embodiment, tissue damage volume can be determined using commercially available software. A particularly suitable software platform that can be used is INTELLISPACE PORTAL (ISP) (commercially available from Phillips Healthcare). INTELLISPACE PORTAL with the Liver Analysis tool is particularly suitable. The TDVS score can be used with a measurement of damage by ischemia/reperfusion (SV) to determine tissue injury magnitude score (TIMS) using equation (II):

$$((TDVS_{tot})^{0.25})((SV_{0.9})^{0.25})=TIMS \qquad (II)$$

where $TDVS_{tot}$ represents the total TDVS and SV represents the damage by ischemia/reperfusion.

The embodiments described herein include a metric to quantify the magnitude (physical volume) of damaged tissue sustained by an injured patient by measuring the volume and type of injured tissue in trauma patients. Through analysis of patient clinical factors, it has been discovered that the volume of tissue injury can be used to determine systemic inflammation and organ failure in these multiply injured patients. Quantifying the magnitude of soft tissue injury using medical imaging and its application as a clinical index is a novel concept, and can be used in every trauma patient in the world, much like other clinical metrics such as blood pressure, heart rate, respiratory rate, red blood cell count, Injury Severity Score, Glasgow Coma Scale, and other measureable clinical indicators.

EXAMPLES

Example 1

In this Example, tissue damage volumes were analyzed to determine multiple organ failure.

Figure 3:
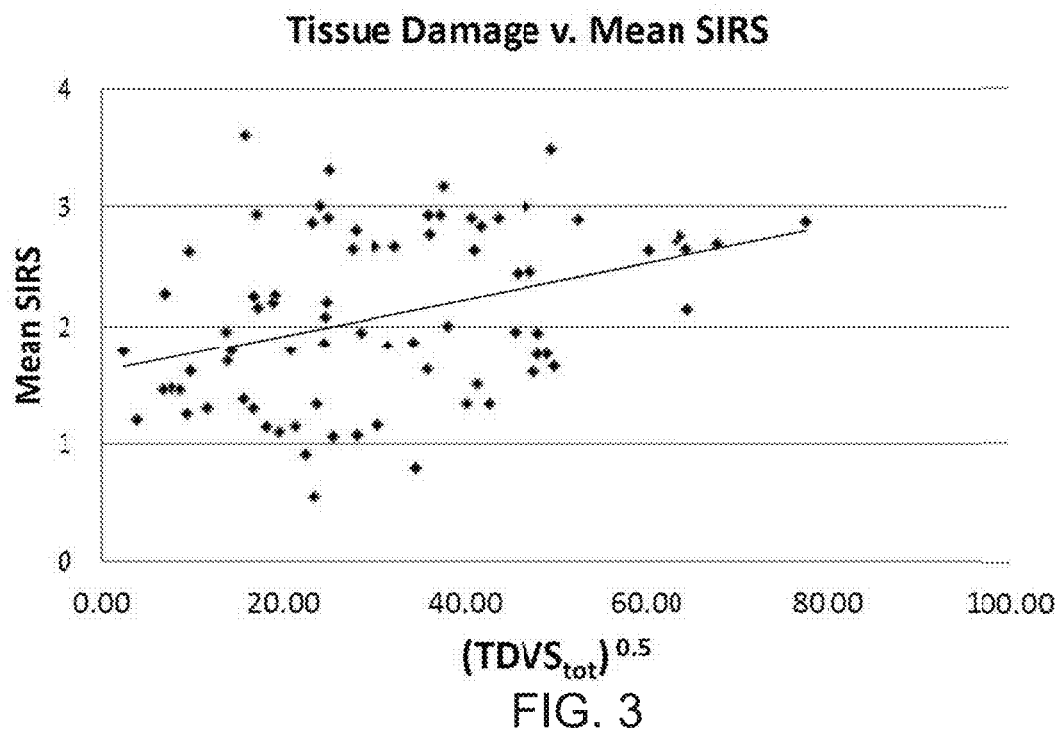
FIG. 3 is a graph depicting mean systemic inflammatory response syndrom (SIRS) as a function of the square root of a tissue damage volume score.
Figure 4:
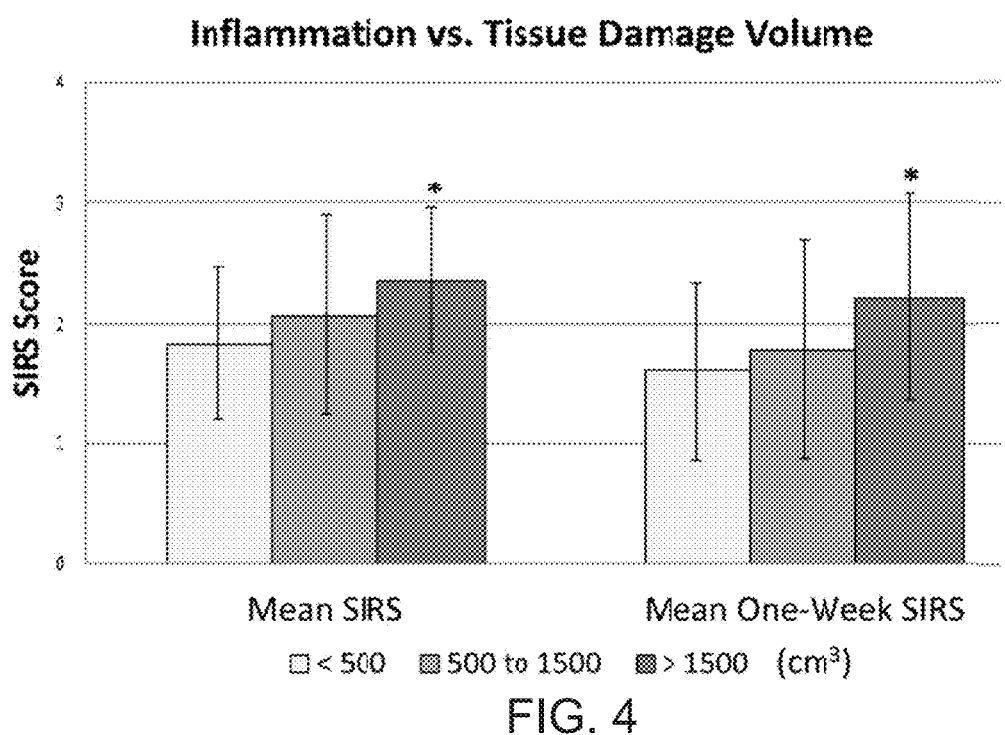
FIG. 4 is a graph depicting mean SIRS scores initially and at one week as a function of different ranges of the tissue damage volume score.

The process of calculating the total body soft tissue damage volume score was completed on over 81 patients. FIG. 3 is a graph showing the correlation between mean SIRS scores and the square root of the tissue damage volume score (TDVS). FIG. 4 is a graph of the SIRS score for different mean TDVS scores initially and at one week.

Figure 5:
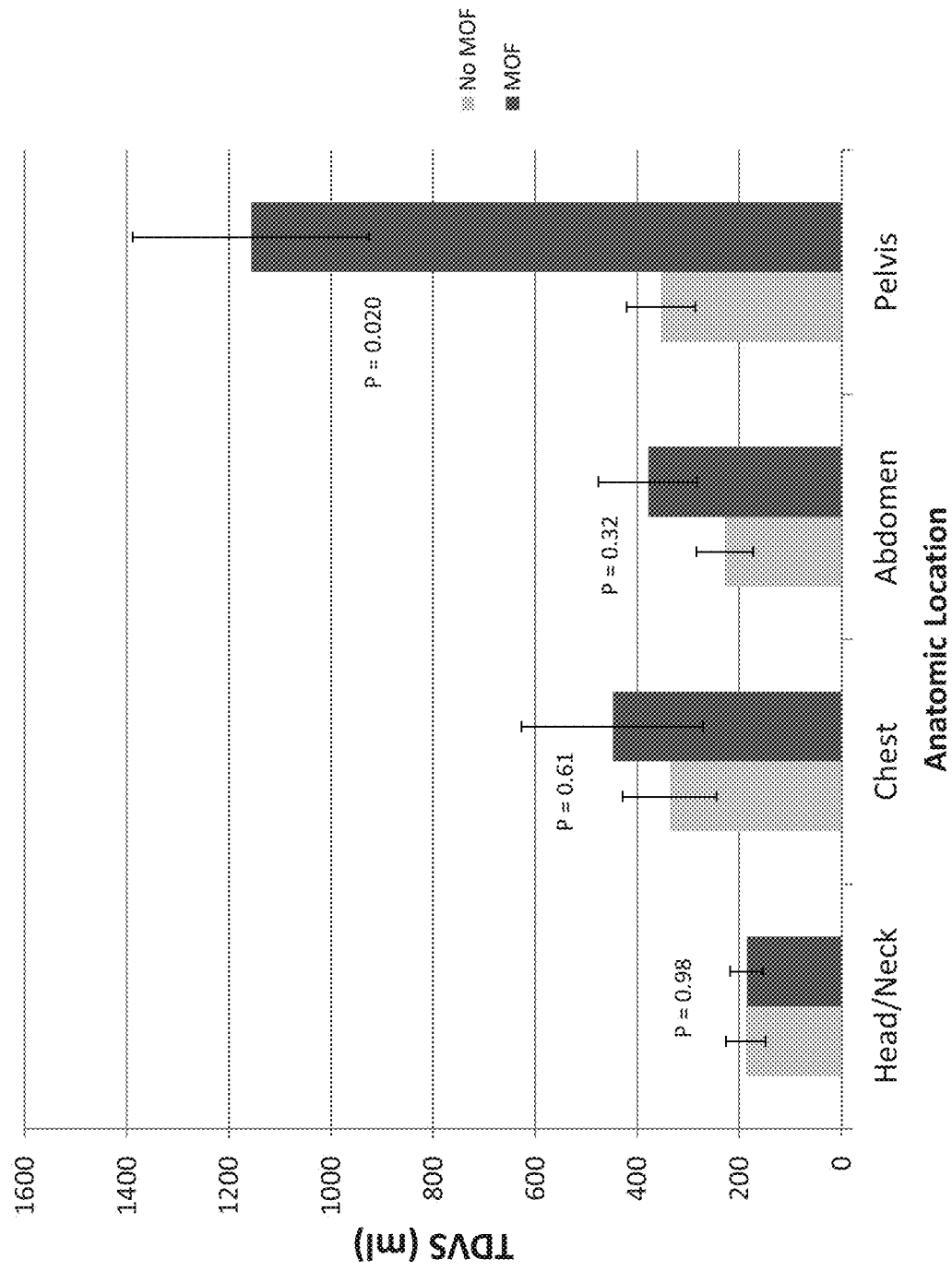
FIG. 5 is a graph depicting multiple organ failure according to tissue damage volume.
Figure 6:
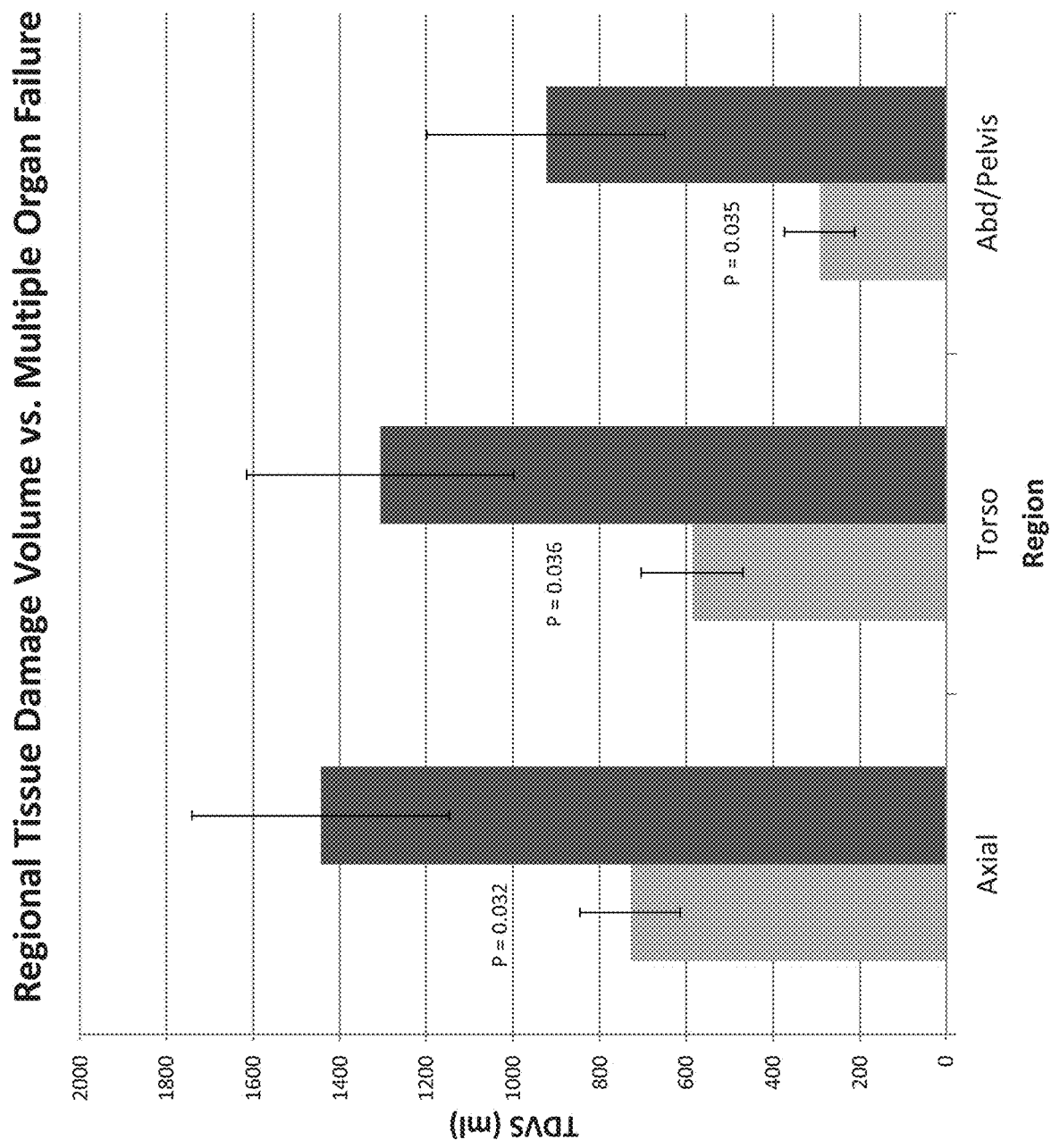
FIG. 6 is a graph depicting multiple organ failure according to regional tissue damage volume.

Tissue damage volumes of the axial anatomy (head, neck, thorax, abdomen, and pelvis) were determined in 74 multiply injured patients. Anatomic regions were broken down into head/neck, chest, abdomen, and pelvis. Combination regions including abdominopelvis, torso (chest, abdomen, pelvis) and axial (all anatomic locations: head/neck, chest, abdomen, pelvis) were also analyzed. As depicted in FIG. 5 for anatomic regions, patients with large volume pelvis injuries are at risk for organ failure. With combined anatomic locations into regions, adding the CT-based tissue damage volumes demonstrated that differences in volumetric measurements extrapolated into organ failure risk (FIG. 6).

Example 2

In this Example, tissue damage volumes were analyzed to determine systemic inflammation.

Specifically, systemic inflammation as defined by the Systemic Inflammatory Response Syndrome (SIRS) was determined by analyzing tissue damage volumes. Patients were categorized into patients that had either high magnitude SIRS (a SIRS score of at least 4 for at least two days) or sustained SIRS (a SIRS score of ≥3 for at least 5 days).

Figure 7A:
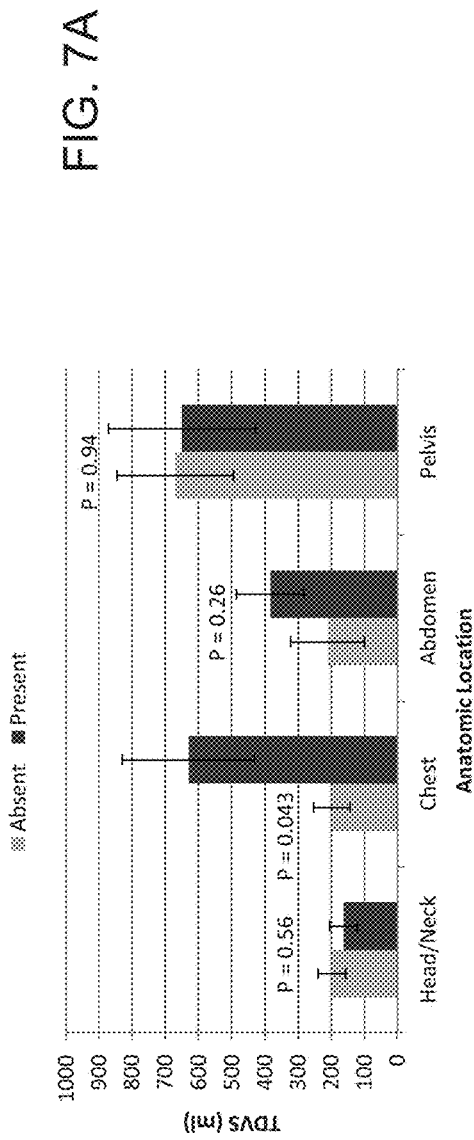
FIGS. 7A & 7B are graphs depicting high magnitude systemic inflammation according to tissue damage (FIG. 7A) and sustained systemic inflammation according to tissue damage (FIG. 7B).
Figure 7B:
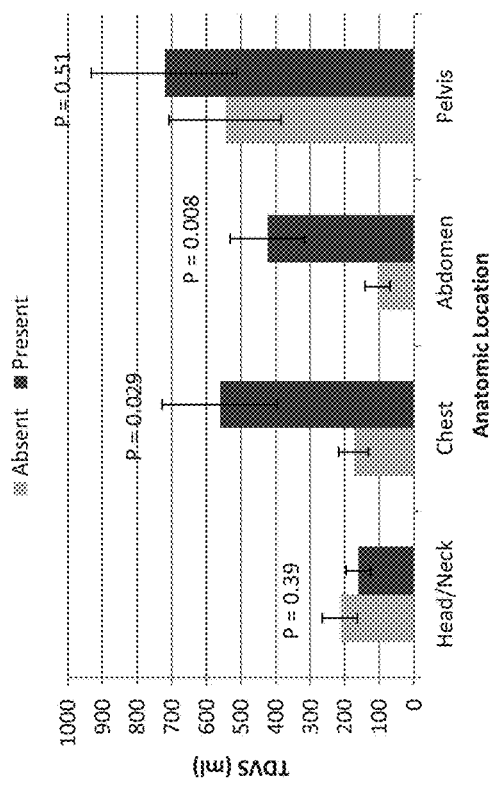

As depicted in FIG. 7, chest injury was the main predictor of both high magnitude SIRS (FIG. 7A) and sustained SIRS (FIG. 7B).

It should be appreciated that one or more aspects of the present disclosure may transform a general-purpose computing device into a special-purpose computing device when configured to perform the functions, methods, and/or processes described herein.

This written description uses examples to disclose various implementations to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining a risk for multiple organ failure in an injured patient, the method comprising:
   obtaining a medical image of a plurality of tissue injuries, wherein the plurality of tissue injuries comprises an axial anatomy tissue injury;
   providing the medical image to an analytical system comprising: a memory device and a processor communicatively coupled to the memory device, and wherein the analytical system is programmed to:
   calculate a volume measurement for each of the plurality of tissue injuries,
   wherein the volume calculation is $V=(4/3)r^3\pi$ it and wherein r is determined by averaging three diameter measurements of the tissue injury and dividing by 2, the three diameter measurements consist essentially of a first measurement in the maximum axial dimension along the 804 axis, a second measurement perpendicular to the first measurement along the 802 axis, and a third measurement in the craniocaudal direction along the 806 axis;
   sum the volume measurement for each of the plurality of tissue injuries to determine a total volume of tissue injury; and
   determine a risk for multiple organ failure of the injured patient based on the total volume of tissue injury compared to a series of predetermined thresholds of total volume of tissue injury that correlate to different degrees of risk for multiple organ failure of the injured patient,
   wherein determining the risk for multiple organ failure of the injured patient comprises determining the risk for multiple organ failure of the injured patient based on a total volume of the axial anatomy tissue injury compared to a series of predetermined thresholds of total volume of axial tissue injury that correlate to different degrees of risk for multiple organ failure of the injured patient.

2. The method of claim 1, wherein the medical image is selected from the group consisting of a radiographic image, a computed tomography (CT) scan, a magnetic resonance image (MRI), an x-ray, an ultrasound image, and combinations thereof.

3. The method of claim 1, wherein the total volume of the axial anatomy tissue injury is from 1100 ml to 1750 ml,
   wherein determining the risk for multiple organ failure of the injured patient comprises determining the risk for multiple organ failure of the injured patient based on the total volume of the axial anatomy tissue injury being from 1100 ml to 1750 ml.

4. The method of claim 1, wherein the plurality of tissue injuries comprises a torso tissue injury, wherein determining the risk for multiple organ failure of the injured patient comprises determining the risk for multiple organ failure of the injured patient based on a total volume of the torso anatomy tissue injury compared to a series of predetermined thresholds of total volume of torso tissue injury that correlate to different degrees of risk for multiple organ failure of the injured patient.

5. The method of claim 4, wherein the total volume of the torso tissue injury is from 1000 ml to 1650 ml, wherein determining the risk for multiple organ failure of the injured patient comprises determining the risk for multiple organ failure of the injured patient based on the total volume of the torso tissue injury being from 1000 ml to 1650 ml.

6. The method of claim 1, wherein the plurality of tissue injuries comprises an abdominopelvis tissue injury, wherein determining the risk for multiple organ failure of the injured patient comprises determining the risk for multiple organ failure of the injured patient based on a total volume of the abdominopelvis anatomy tissue injury compared to a series of predetermined thresholds of total volume of abdominopelvis tissue injury that correlate to different degrees of risk for multiple organ failure of the injured patient.

7. The method of claim 6, wherein the total volume of the abdominopelvis tissue injury is from 650 ml to 1200 ml, wherein determining the risk for multiple organ failure of the injured patient comprises determining the risk for multiple organ failure of the injured patient based on the total volume of the abdominopelvis tissue injury being from 650 ml to 1200 ml.

\* \* \* \* \*